Figure 1:
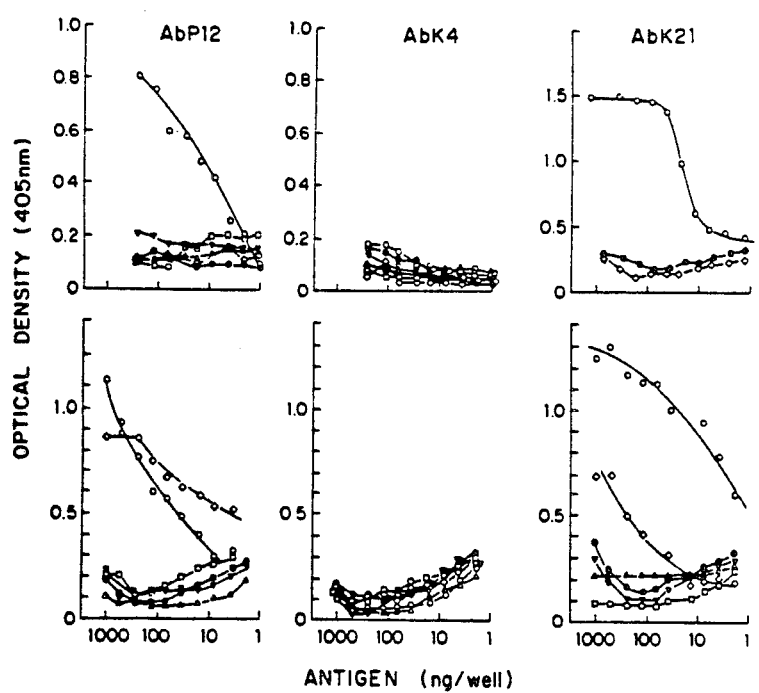

United States Patent [19]

Rettig et al.

[11] Patent Number: 4,762,800
[45] Date of Patent: Aug. 9, 1988

[54] MONOCLONAL ANTIBODIES TO CELL SURFACE ANTIGENS OF HUMAN TERATOCARCINOMAS

[75] Inventors: Wolfgang Rettig; Carolos Cordon-Cardo, both of NY, N.Y.; Herbert F. Oettgen, New Canaan, Conn.; Lloyd J. Old, New York, N.Y.; Kenneth O. Lloyd, New York, N.Y.; Jennifer Ng, New York, N.Y.

[73] Assignee: Sloan-Kettering Institute for Cancer Research, New York, N.Y.

[21] Appl. No.: 604,080

[22] Filed: Apr. 26, 1984

[51] Int. Cl.$^4$ .................... C12N 5/00; G01N 33/534; G01N 33/533; A61K 39/395
[52] U.S. Cl. .................... 436/548; 435/240.27; 530/387; 935/104; 935/110
[58] Field of Search .................... 435/68, 240, 192.2, 435/7; 436/548; 935/104, 110; 530/387

[56] References Cited

U.S. PATENT DOCUMENTS 4,563,445 1/1986 Feizi et al. .................... 536/17.2

OTHER PUBLICATIONS

Blaineau et al, "The Glycosidic Antigen Recognized by a Novel Monoclonal Antibody. 75.12, is Developmentally Regulated", EMBO Journal 2(12) pp. 2217–2222 (1983).

Kannagi et al, "New Globoseries Glycosphingolipids in Human Teratocarcinoma Reactive with the Monoclonal Antibody Directed to a. . ." Journal of Biochemistry 258(14) pp. 8934–8942 (1983).

Miyauchi et al, "A New Fucosyl Antigen Expressed on Colon Adenocarcinoma and Embryonal Carcinoma Cells" Nature 299 pp. 168–169 (1982).

Gooi et al, "A Marker of Human Foetal Endoderm Defined by a Monoclonal Antibody involves Type I Blood Group Chains" Molecular Immunology 20(6) pp. 607–613 (1983).

Gooi et al, "Stage-Specific Embryonic Antigen Involves Alpha 1-3 Fucosylated Type 2 Blood Group Chains" Nature 292 pp. 156–158 (1981).

Gooi et al, "Marker of Peripheral Blood Granulocytes and Monocytes of Man Recognized by two Monoclonal Antibodies" European Journal of Immunology 13 pp. 306–312 (1983).

Kannagi et al, "Stage-Specific Embryonic Antigens (SSEA-3 and -4) are Epitopes of a Unique Globo-Series Ganglioside" EMBO Journal 2(12) pp. 2355–2361 (1983).

*Primary Examiner*—John E. Tarcza
*Attorney, Agent, or Firm*—John P. White

[57] ABSTRACT

Antibody-producing hybridoma cell lines made by fusion of NS/1 cells with spleen cells of mice after immunization with human teratocarcinoma cells are presented. Monoclonal antibodies from these cell lines recognize the K4, K2 and P12 antigenic systems and are thus useful in detecting and differentiating between normal and cancerous cells. These monoclonal antibodies are especially useful in pathologic analysis of human tumors, especially teratocarcinomas.

6 Claims, 2 Drawing Sheets

MONOCLONAL ANTIBODIES TO CELL SURFACE ANTIGENS OF HUMAN TERATOCARCINOMAS

This present invention was wholly or partially made with funds provided by the Department of Human Health and Services under Grant No. CA 08748 and CA 34039. Accordingly, the United States Government has certain rights in this invention.

This invention concerns monoclonal antibodies to cell surface antigens of teratocarcinomas. The antibodies may be used to detect teratocarcinoma cells and to distinguish different histological cell types within the tumor. These monoclonal antibodies are especially useful in pathologic analysis of tumors including human teratocarcinoma and for immunotherapy of human tumors.

BACKGROUND

Cultured cell lines have been used to generate and analyze monoclonal antibodies to several malignant cell types lines including melanoma (Dippold, W.G., et al. (1980) Proc. Nat'l. Acad. Sci. (Wash.) 77:6114–6118), astrocytoma (Cairncross, J.G., et al. (1982) Proc. Nat'l. Acad. Sci. (Wash.) 79:5641–5645) and certain epithelial cancers (Ueda, R., et al. (1981) Proc. Nat'l. Acad. Sci. (Wash). 78:5122–5126; Fradet, Y., et al. (1984) Proc. Nat'l. Acad. Sci. (Wash.) 81:224–228; and Mattes, M.J., et al. (1984) Proc. Nat'l. Acad. Sci. (Wash.) 81:568–572). In each case it has been found that the cells selectively express surface antigens which are characteristic of the particular cell type. Since the presence of unique surface antigens is of diagnostic and therapeutic significance, antigens restricted to other malignant cells have been studied.

Some information is available concerning surface antigens of teratocarcinoma cells. It is known for instance that teratocarcinoma cells display a characteristic pattern of cell surface carbohydrates (Solter, D., et al. (1978) Proc. Nat'l. Acad. Sci. (Wash.) 75:5565–5569). Coordinated changes in the expression of a group of biosynthetically related carbohydrate sequences have been demonstrated during the embryonal development in the mouse and during certain stages of cellular differentiation in human teratocarcinoma (Kapadia, A., et al. (1981) Exp. Cell Res. 131:185–195; Teshima, S., et al. (1984) Lab. Inves. 50:271). Also, a shift in glycolipid synthesis from the globo-series to the lacto-series during differentiation has been propsoed by Kannagi et al. (Kannagi, R., et al. (1983) Embo. J. (1983) 2:2355–2361) as a characteristic feature of human teratocarcinoma cells. Accordingly, monoclonal antibodies capable of recognizing surface antigens of teratocarcinoma cells have been sought.

SUMMARY

Hybridoma cell lines have been made by the method of Kohler and Milstein (Kohler, G., et al. (1975) Nature 256:495–496) using splenocytes of BALB/c mice immunized with human teratocarcinoma cells. Three hybridoma cell lines were selected. Monoclonal antibodies produced by these cell lines, designated AGK4, AGK21 and AGP12, recognize three distinct human teratocarcinoma antigenic systems, designated K4, K21 and P12.

Since it has been found that the presence of antigenic systems K4, K21 and P12 differs between normal and cancer cells, monoclonal antibodies recognizing these surface antigens may be used to differentiate between normal and cancerous cells and to detect human tumor cells, especially teratocarcinoma cells. Excised tumor specimens and body fluids (including blood, urine and amniotic fluid) urine can be tested with the monoclonal antibodies AGK4, AGK21 and AGP12, to determine the presence of antigens K4, K21 and P12. The extent of reaction between antigenic system and antibody between antigenic system and antibody which can be measured by methods known in the art, indicates the quantity and nature of antigens present and hence the presence of cancerous cells. The antibodies of the present invention are also useful in immunoimaging of tumors in vivo when tagged with fluorescent, radioactive or chromophoric groups and in immunotherapy when tagged with toxins, chemotherapeutic agents or radioisotopes.

Details

Availability of Cell Lines

Hybridoma cell lines producing the monoclonal antibodies of the present invention have been deposited prior to filing of the present application at the American Type Culture Collection, Bethesda, Maryland and will be made available to the public during pendancy of any patent issuing therefrom in accordance with the Budapest Treaty. The monoclonal antibodies bear the following designations:

| Herein Designated | ATCC |
| --- | --- |
| Ab K4 | HB 8550 |
| Ab K21 | HB 8549 |
| Ab P12 | HB 8551 |

Deposit is for the purpose of enablement only and is not intended to limit the scope of the present invention. Clones of these cell lines and other cell lines derived therefrom are considered to be foreseen by the present invention.

Cell lines and cell culture

The panel of human cell cultures listed in Table 1 has been described previously (Dippold, W. G., et al. (1980) Proc. Nat'l. Acad. Sci. (Wash.) 77:6114–6118; Cairncross, J. G., et al. (1982) Proc. Nat'l. Acad. Sci. (Wash.) 79:5641–5645; Ueda, R., et al. (1981) Proc. Nat'l. Acad. Sci. (Wash). 78:5122–5126; Fradet, Y., et al. (1984) Proc. Nat'l. Acad. Sci. (Wash.) 81:224–228; and Mattes, M. J., et al. (1984) Proc. Nat'l. Acad. Sci. (Wash.) 81:568–572). 833KE, is a cell line derived from a testicular teratocarcinoma. Tera-1 and Tera-2, cell lines derived from testicular teratocarcinomas, are on deposit at the Cell Bank at Sloan-Kettering Institute, New York, N.Y. Five gestational choriocarcinoma cell lines were used in this study: GCC-SV(c), Lu75(c), SCH, BeWo, JAR and JEG-3. Cell culture conditions have been described (Dippold, W.G., et al. (1980) Supra.

Glycoproteins and glycolipids

Blood group glycoproteins isolated from ovarian cyst fluids have been described (Lloyd, K. O., et al. (1983) Immunology, 17:537–541). Among these samples, OG is rich in non-fucosylated precursor structures, the Le$^a$ preparation also carries blood group X structures and the Le$^b$ sample also contains Y blood group structures. Lacto-N-tetraose-bovine serum albumin (LNT-BSA)

and lacto-N-neotetraose-BSA (LNneoT-BAS) conjugates were LNneoT-BAS was provided as its N-acetylneuraminyl derivative and was desialylated by mild acid hydrolysis (0.1N at 80° C. for 1 hr) before use. α1-Acid glycoprotein, fetuin and transferrin were purchased from Sigma Chemical Co. Glycophorin and asialoglycophorin were prepared from human red cells according to the procedure of Springer (Springer, G.F., et al. (1966) Biochemistry 5:3254:3272). CEA may be obtained from blood group-related glycolipids (Table 1) have been described (Hansson, G. C., et al. (1983) J. Biol. Chem. 258:4091-4097). The major ganglioside from teratocarcinomas (GL-7: NeuAcα2→3 Galβ1→3GalNacβ1→3Galβ1→4 Glcβ1→1Cer) was obtained as a partially purified sample.

Generation of monoclonal antibodides

Antibodies AbK4 and AbK21 were derived from immunizations of (BALB/c X C57BL/6)F1 mice with Tera-1 cells following published procedures (Dippold, W.G., et al. (1980) Supra). Antibody AbP12 was derived after immunization with a membrane fraction of human placental tissue. Spleen cells were fused with mouse myeloma MOPC-21 NS/1 cells and antibody-producing clones were isolated by repeated subcloning. Hybridoma cells were injected subcutaneously into nu/nu mice (Swiss background) and serum from mice with progressively growing tumors was used as a source of antibody for serological and biochemical studies. Antibody subclass was determined by double diffusion in agar with anti-Ig heavy chain-specific antisera (Bionetics, Kensington, MD).

Serological procedures

Rosetting assays for the detection of cell surface antigens on cultured cells using rabbit anti-mouse Ig or goat anti-mouse μ chain antibodies conjugated to human O erythrocytes, were performed according to methods described previously (Dippold, W. G., et al. (1980) Proc. Nat'l. Acad. Sci. (Wash.) 77:6114–6118; Cairncross, J. G., et al. (1982) Proc. Nat'l. Acad. Sci. (Wash.) 79:5641–5645; Ueda, R., et al. (1981) Proc. Nat'l. Acad. Sci. (Wash). 78:5122–5126; Fradet, Y., et al. (1984) Proc. Nat'l. Acad. Sci. (Wash.) 81:224–228; and Mattes, M. J., et al. (1984) Proc. Nat'l. Acad. Sci. (Wash.) 81:568–572). 1,5). Non-adherent target cells were prepared for the rosetting assay by the concanavalin A method of Mattes et al. For hemagglutination assays see Ref. Anger, B. R., et al. (1982) Hybridoma 1:139–146. Absorption tests were carried out as described (Dippold, W. G., et al. (1980) Supra). Heat stability of antigenic determinants was assessed by heating target cells to 100° C. for 5 min prior to an absorption test. Susceptibility to enzyme digestion was determined by incubation of target cells with trypsin (Sigma Co., 0.5 mg/ml in DPBS, 30 min at 37° C.) or neuraminidase (Calbiochem Co., Vibrio cholerae neuraminidase, 0.1 IU/ml in DPBS, 30 min at 37° C.) before the absorption test. Blocking experiments were performed to determine whether the epitopes recognized by AbK4 and AbK21 are related. These assays were based on the observation that rabbit anti-mouse Ig indicator cells attached to the target cells and for the titration endpoint. Inhibition of antibody reactivity with target cells in the MHA assay was tested as described (Mattes, M. J. et al. (1984) Supra) using choloroform/methanol extracts of Tera-1 cells and the purified glycoproteins listed in Table 4.

Immunofluorescence assays

Frozen sections (5 μm) of tissues were air dried, fixed for 5 min in 3.7% formaldehyde in PBS, washed and incubated for 1 hr with undiluted hybridoma culture supernatant or a 1/50 dilution of nu/nu serum. The slides were washed and incubated for 30 min with a 1/40 dilution of fluorescein-conjufated goat anti-mouse Ig (Cappel Laboratories, Cochranville, PA), washed again and wet-mounted in 90% glycerol in PBS.

Immunoprecipitation procedures

Cells were metabolically labeled with [$^3$H] glucosamine, [$^{35}$S]methionine, or [$^3$H]fucose as described (Dippold, W. G., et al. (1980) Supra). For sulfate-labeling, cells were cultured in the presence of [$^{35}$S]O$_4$ (50u-Ci/ml) in sulfate-free medium (Fisher's medium, GIBCO Laboratories) for 6–12 hr. Preparation of NP40 lysates and their fractionation on concanavalin A-sepharose has been described (Dippold, W. G., et al. (1980) Proc. Nat'l. Acad. Sci. (Wash.) 77:6114–6118; Cairncross, J. G., et al. (1982) Proc. Nat'l. Acad. Sci. (Wash.) 79:5641–5645; Ueda, R., et al. (1981) Proc. Nat'l. Acad. Sci. (Wash). 78:5122–5126). Immunoprecipitation and SDS-polyacrylamide gel electrophoresis (SDS-PAGE) procedures have also been described (1). In some experiments, cell lysates were heated to 100° C. for 5 min, precipitates were removed by centrifugation and supernatants were used for immunoprecipitation. Alternatively, lysates were incubated with neuraminidase (0.1 IU/ml, 60 min at 37° C.) heated to 100° C. for 5 min to inactivate the enzyme, and used for immunoprecipitation tests. Treatment of immunoprecipitates with Chondroitinase ABC (Miles, 20 mM in DPBS) was carried out at 37° C. for 60 min, immunoprecipitates were washed once in DPBS, extracted and analyzed by SDS-PAGE.

Enzyme-linked immunoassay

Purified glycolipids were adsorbed to the wells of Falcon 3040 microtest plates and the enzyme-linked immunoassay was performed as described (Lloyd, K. O., et al. (1983) Immunology 17:537–541). A similar method was used for testing glycoproteins except that the antigens were dissolved in water and added to the wells in the range 1–2,000 ng/well. The plates were subsequently drived in vacuo over P$_2$O$_5$.

Monoclonal antibodies

Figure 2:
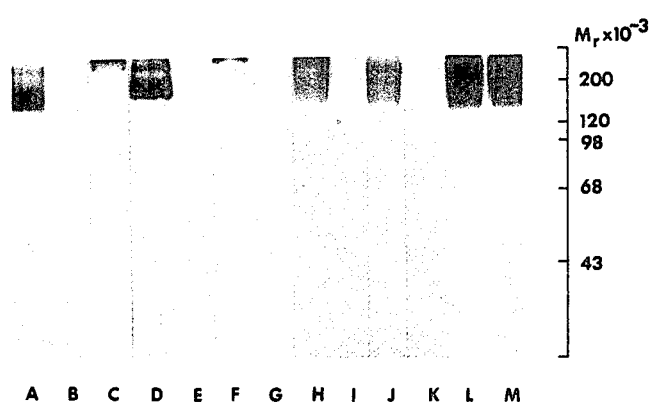

Monoclonal antibodies AbK4 and AbK21 were derived from immunization of mice with Tera-1 human teratocarcinoma cells. AbP12 was derived after immunization with human placental tissue. AbK4 is an IgG$_1$ antibody, AbK21 and AbP12 are IgM antibodies. Antibody specificity was determined with the MHA assay on a panel of 150 established human cell lines and short term cultures of fibroblasts and kidney epithelial cells (Table 1), as well as by immunofluorescence analysis of normal fetal and adult human tissues (Table 2) and tumor specimens (Table 3). Antigens detected by the antibodies were characterized by SDS-polyacrylamide gel electrophoresis of immunoprecipitates obtained from radiolabeled cell extracts (FIG. 2). Enzyme-linked immunoassays with purified glycoproteins and glycolipids permitted identification of the carbohydrate determinants recognized by antibodies AbK21 and AbP12 (FIG. 1). The results show that the antibodies defined three distinct cell surface antigen systems.

K4 antigenic system

Among 165 cultures of normal and malignant cells tested by MHA assay, only Tera-1, Tera-2 and 833KE, the cell lines derived from testicular teratocarcinomas, were K4 positive (titers $0.2-1.0 \times 10^{-6}$). All other cells were unreactive at a 1:250 dilution of nu/nu mouse serum. The restricted distribution of K4 on cultured cells was confirmed by absorption tests with teratocarcinoma cells, 2 colon cancers, 2 renal cancers, 2 bladder cancers, 2 lung cancers, 2 breast cancers, 2 melanomas, 2 astrocytomas and EBV-transformed B-cells. Only teratocarcinoma cells and one colon cancer, HT-29, absorbed AbK4 reactivity.

Immunofluorescence studies on normal and malignant tissues revealed that K4 is expressed solely on epithelial cells of the fetal and adult gastrointestinal tract and some other fetal tissues. K4 staining was also found in specimens of teratocarcinoma (Teshima, S., et al. (1984) Lab. Inves. 50:271 and Kannagi, R., et al. (1983) Embo. J. 2:2355-2361) and subsets of other malignancies. The antigenic determinant detected by AbK4 is heat stable and resistant to proteinase and trypsin. However, neuraminidase treatment of teratocarcinoma cells prior to an MHA assay completely abolished K4 reactivity. Immunoprecipitation analysis of radiolabled NP40 lysates of Tera-1, Tera-2 and 833KE cells revealed the nature of the K4 antigen. When [$^3H$]glucosamine labeled extracts were used, a major component of Mr 160-200,000 was specifically precipitated (FIG. 1). A similar pattern was obtained from [$^{35}S$]methionine-labeled material eluted from a concanavalin A-Sepharose column. These glycoprotein components are also sulfated as shown by immunoprecipitation using [$^{35}S$]O$_4$ cell lysates. The SDS-PAGE pattern of the sulfate-labeled components consisted of a broad smear starting at the origin which suggests substantial heterogeneity in the molecular weight of K4 antigens. The antigens could still be immunoprecipitated after heating the cell lysates to 100° C. for 5 min. In agreement with the loss of serological reactivity after treatment of target cells with neuraminidase, no labeled components were precipitated by AbK4 after incubation of Tera-1 extracts with neuraminidase. Incubation of immunoprecipitates with Chondroitinase ABC before electrophoretic analysis did not affect the apparent size of the precipitated K4 antigens. These biochemical properties suggest that AbK4 recognizes a sialylated carbohydrate determinant on high-molecular weight, sulfated glycoproteins. In an attempt to identify the K4 determinant, a series of known glycoproteins (ceruloplasmia, -acid glycoprotein, fetuin, transferrin, glycophorin, asialoglycophorin, CEA and N-acetylneuraminyl (Cairncross, J. G., (1982) Proc. Nat'l. Acad. Sci. (Wash.) 79:5641–5645; Ueda, R., et al. (1981) Proc. Nat'l. Acad. Sci. (Wash.) 78:5122–4126; Fradet, Y., et al. (1984) Proc. Nat'l. Acad. Sci. (Wash.), 81:224–228; Mattes, M. J., et al. (1984) Proc. Nat'l. Acad. Sci. (Wash.), 81:568–572 and Solter, D., et al. (1978) Proc. Nat'l. Acad. Sci. (Wash.), 75:5565–5569) LNneoT-BAS) and glycolipids (see FIG. 1, and also GL-7 and brain gangliosides) was tested in an enzyme-linked immunoassay and by MHA inhibition assay. AbK4 did not react with any of these substances, except for a weak reaction with CEA, and appears to define a novel carbohydrate sequence, the precise structure of which remains to be determined.

K21 antigenic system

Only two cultured cell types express the K21 antigen: teratocarcinomas (with titers of $0.2-1.0 \times 10^{-7}$) and, at 100 to 1,000-fold lower levels, cultures of normal and malignant kidney epithelial cells. The 147 other cell lines tested were K21 negative. Immunofluorescence studies on a wide range of normal tissues showed that K21 is restricted to epithelial cells of the fetal intestinal tract and fetal bronchus. No other fetal and no adult tissue was stained with AbK21. In the panel of 36 tumor specimens tested, only a subset of testicular teratocarcinomas (Solter, D., et al. (1978) Supra; Kapadia, A., et al. (1981) Exp. Cell Res., 131:185–195; Teshima, S., et al. (1984) Lab. Inves. 50:271; Kannagi, R., et al. (1983) Embo. J., 2:2355-2361) was K21 positive. The antigenic determinant recognized by AbK21 is heat stable and resistant to trypsin and proteinase. Incubation of teratocarcinoma cells with neuraminidase increased reactivity with AbK21 by more than 10-fold. Cultured cells that were K21 negative by both direct MHA assay and absorption tests (SK-MEL-28, SK-PN-Dw, SK-CO-15, SW1417) became K21 positive after neuraminidase treatment (titers $1 \times 10^{-4}$ to $1 \times 10^{-5}$). Immunoprecipitation experiments with [3H]glucosamine and [$^{35}S$])$_4$ labeled teratocarcinoma cells revealed that the K21 determinants are carried on high molecular weight sulfated glycoproteins similar to those bearing K4 structures. However, no precipitates were detected using total or Concanavalin A-sepharose fractionated extracts of [$^{35}S$] methionine labeled cells. Also, in contrast to the K4 antigenic system, neuraminidase treatment of Tera-2 cell lysates prior to immunoprecipitation produced an increase in the amount and a shift in the molecular weight range of the precipitated glycoproteins. Similar to K4, neither boiling of cell extracts nor incubation with chondroitinase ABC led to substantial changes in the SDS-PAGE pattern of K21 immunoprecipitates. The antigenic determinant recognized by AbK21 was identified by ELISA tests and by inhibition assays using the purified glycoproteins to block reactivity with Tera-1 target cells in the MHA assay. AbK21 reacted strongly with purified glycoproteins and synthetic glycopeptides carrying the lacto-N-tetraose sequence (FIG. 2). Lacto-N-neotetraose-bearing glycoproteins were negative and of the other antigens tested only Le$^a$ glycoproteins showed weak reactivity. All glycolipids tested, including lacto-N-tetraose ceramide, were negative by ELISA analysis. The results of the serological and biochemical studies indicate that AbK4 and AbK21 identify different antigenic determinants. This was confirmed by blocking experiments, i.e. reactivity of AbK4 with Tera-1 cells (detected by the rabbit anti-mouse Ig MHA assay) was not inhibited by pre-incubation with an excess of AbK21 and, conversely, AbK21 rosetting (detected by the goat anti-mouse-u chain MHA assay) was not inhibited by an excess of AbK4. As both antibodies precipitate similar glycoproteins, sequential precipitation experiments were performed to determine whether individual glycoproteins carry both antigenic determinants. Preclearing of a Tera-2 cell lysate with either antibody only slightly affected the amount of radiolabeled material precipitated subsequently using the alternate antibody (FIG. 1). These results suggest that the K4 and K21 antigenic determinants do not generally reside on the same population of glycoproteins.

P12 antigenic system

This antibody was chosen for analysis because it stains certain areas of teratocarcinomas but is unreactive with secitons of normal adult testis. It was derived from immunizations with a membrane preparation of placental tissue. The trophoblast membrane is P12 negative but fetal granulocytes, which were probably contained in the tissue extract used for immunization, are strong P12 expressors and could account for the formation of AbP12. The expression of P12 antigen on cultured cells is essentially non-overlapping with K4 and K21. Subsets of choriocarcinoma and epithelial cancers, leukemias and neuroblastomas express P12 whereas the teratocarcinoma cell lines, melanomas, astrocytomas and fibroblast cultures are antigen-negative. The characteristics of AbP12 reactivity (resistance to boiling, trypsin and proteinase treatment) indicated that AbP12 recognizes a carbohydrate determinant. The results of the ELISA analysis and the MHA inhibition tests show that the antibody is directed against the lacto-N-fucopentaose III carbohydrate sequence: all glycoproteins and X-5 glycolipid share this carbohydrate structure. Immunocytochemical studies show that this antigen is not restricted to teratocarcinoma but is also found in various normal tissues and other tumor types. The biochemical nature of the molecules carrying the P12 determinant in fresh teratocarcinoma tumors could not be determined. As the cultured teratocarcinoma cells available for this study lacked P12 expression, we analyzed the P12 antigen of MCF-7 breast cancer cells. Using immunoprecipitation tests with [$^3$H]fucose and [$^3$H]glucosamine labeled MCF-7 cell extracts, we demonstrate that AbP12 reacts with high molecular weight glycoproteins (FIG. 1), which have a pI 4.0 as determined by isoelectric focusing.

Specificity of monoclonal antibodies

Two of the antigenic systems described in this study, K4 and K21, are specifically expressed on cultured teratocarcinoma cells and fresh teratocarcinoma specimens and only a few other cell types. The other antigen discussed, P12, has a broader tissue distribution and is also expressed on teratocarcinoma specimens. The epitope recognized by antibody AbK21 is present on the lacto-N-tetraose (LNT) sequence and weak cross-reactivity exists with the Le$^b$ structure. Williams et al. ((1982) Int. J. Cancer 30:731-738) have recently described a monoclonal antibody, LICR LON FC10.2, which reacts with a glycoprotein of Mr 200,000 expressed in human teratocarcinoma cells, which is also specific for lacto-N-tetraose (Gooi, H. C., et al. (1983) Molec. Immuno. 20:607-613). Immunocytochemical studies showed that antibody LICR LON FC10.2 primarily stained fetal intestinal and brochial epithelia and are in agreement with the tissue distribution described here for K21. We have tested a large panel of human cell lines and shown that apart from teratocarcinomas, only cultures derived from normal or malignant kidney epithelium express K21. Neuraminidase treatment induces moderate K21 reactivity on most cell types in culture, indicating the presence of sialylated lacto-N-tetraose sequences on the cells. The glycoproteins carrying the K21 determinant in teratocarcinoma cells have been analyzed in more detail and appear to be highly sulfated glycoproteins. The lacto-N-tetraose sequence may also be present on glycolipids, but preliminary studies have shown that chloroform/methanol extracts of Tera-1 cells do not inhibit AbK21 reactivity with teratocarcinoma cells in the MHA assay. It is possible that AbK21 reacts with epitopes of high molecular weight glycoproteins on teratocarcinomas but with glycolipids in other tissues. Although the antibody reacts with LNT-containing glycoproteins and synthetic glycopeptides it failed to react with purified glycolipids containing the LNT structure in the ELISA studies. It is not clear whether this reflects antigenic differences between the carbohydrate structures present in the glycoprotiens and glycolipids or whether the adsorption of the glycolipids to microtest plates renders the antigenic determinants unreactive to antibody in the solid phase ELISA.

The K4 antigen also appears to be a high-molecular weight, sulfated glycoprotein. Judged by its heat stability, resistance to proteolytic digestion and susceptibility to neuraminidase, the antigenic determinant recognized by AbK4 is probably a sialylated carbohydrate structure which does not correspond to any of the known epitopes on the panel of glycoproteins and glycolipids tested. Since teratocarcinomas express a major neuraminidase-sensitive glycolipid of the globoside series, GL-7 (Kannagi, R., et al. (1983) Embo. J., 2:2355-2361), it was particularly interesting to find that AbK4 did not react with this ganglioside. Antibodies AbK4 and AbK21 detect distinct epitopes which reside on similar but not identical glycoproteins. The K21 determinant is exposed by neuraminidase whereas all K4 reactivity is destroyed by this enzyme. These similarities in tissue distribution for these antigens raise the question of whether K4 represents the sialylated form of K21. This appears unlikely, however, as cell lines that acquire K21 reactivity upon neuraminidase treatment, e.g. SK-MEL-28 and SK-PN-DW, are K4 negative before enzyme treatment as shown by both direct MHA assay and absorption tests. This does not preclude the possibility that K4 represents a sialylated K21 antigen distinguished by an uncommon linkage of the sialic acid residue, which may be unique to teratocarcinomas and other K4 positive cells. A different and more common type of sialylation would account for the K4/K21 cells that become K4/K21 after enzyme treatment. Although the K21 determinant can be unmasked on most cultured cells, there remains a large quantitative difference in the amount K21 expressed on teratocarcinoma cells versus other cell types.

Antibody AbP12 detects the lacto-N-fucopentaose III structure to which various monoclonal antibodies have been prepared (Hakomori, S., et al. (1983) J. Nat'l. Cancer Insti. 71:231-251; Feizi, T., et al. (1981) Trends Biochem. Sci. 6:333-335). This determinant is also referred to as stage-specific embryonic antigen-1 (SSEA-1) (Gooi, H. C., et al. (1981) Nature 292:156-158), and as the blood group X hapten (Hakomori, S., et al. (1974) The antigens pp. 79-140). Here we present a detailed serological analysis of the antigen distribution on a cell line panel. The pattern of P12 reactivity in sections of normal and malignant tumor tissues is in general agreement with findings reported by Fox et al. ((1983) Cancer Res. 43:669-678) for the anti-SSEA-1 antibody. However, P12 expression is found by in normal breast epithelium, but not in brain or spinal cord, the opposite of the findings for SSEA-1. Since certain human tumor cells carry the lacto-N-fucopentaose III determinant on a distinct group of acidic, high-molecular weight glycoproteins, possibly, the P12 positive human teratocarcinomas express this carbohydrate sequence on similar molecules. These immunocytochemical studies on human teratocarcinomas indicate that the expression of K4, K21 and P12 distinguishes different histological cell types within the tumors. The highly restricted distribution of K21 makes this antigen a candidate for immunological imaging of tumors of human teratocarcinoma.

Table 1

Serial dilutions of antibody were tested by MHA assay (starting dilution of antibody 1/250 of nu/nu serum). Reactivity with the cell lines shown on the left is symbolized as follows: ●, postive reaction at antibody dilutions of $1 \times 10^{-4}$ to $1 \times 10^{-7}$; ◑, postive reaction, at antibody dilution of $5 \times 10^{-3}$ to $1 \times 10^{-4}$; 0, no reactivity at starting dilution of antibody.

Low level expression K21 on occasional cells (1–5%) was observed for cultures of 577MF, SK-UT-1, AsPc-1, SK-OV-3, SW-1710 and SK-LC-1.

Antibody AbP12 did not agglutinate human erythrocyte, but antibody activity was absorbed by incubation with erythrocytes of blood groups A,B and O.

Table 2

Immunofluorescence analysis of normal fetal and adult human tissues with mouse monoclonal antibodies. Cryostat sections (5 μm) of fresh frozen tissues were air-dried, fixed with 3.7% formaldehyde in PBS and reacted with monoclonal antibody and FITC conjugated rabbit anti-mouse Ig.

Results are indicated as follows: ●, positive immunofluorescence; O, negative reaction; ◐, only a subpopulation of cells is stained.

a. P12 staining of granulocytes, macrophages and histocytes was found in most tissue sections.
b. K4 reactivity in fetal gonads were restricted to a small subpoplulation of cells.
c. Strong reactivity with AbP12 was seen in the distal and collecting tubules. Glomeruli, proximal tubules and other structures were negative.
d. Some astrocytes showed K4 reactivity and in some areas of the fetal brain AbK4 and AbK21 produced a filamentous staining pattern.

Table 3

Immunofluorescence analysis of human tumor tissues with mouse monoclonal antibodies. Cryostat sections (5 μm) of fresh frozen tissues were air-dried, fixed with 3.7% formaldehyde in PBS and reacted with monoclonal antibody and FITC conjugated rabbit anti-mouse Ig.

TABLE 1

Reactivity of monoclonal antibodies with cultured human cells and cell lines.

| Cells | Monoclonal Antibody | | | Cells | Monoclonal Antibody | | |
|---|---|---|---|---|---|---|---|
| | K4 | K21 | P12 | | K4 | K21 | P12 |
| Teratocarcinomas | | | | Melanomas | | | |
| Tera-1,Tera-2, 833KE | ●●● | ●●● | 000 | SK-MEL-13,-23,-28,-31, | 0000 | 0000 | 0000 |
| Malignant Teratoma | | | | -37,-41,-94,-131, | 0000 | 0000 | 0000 |
| 577M | 0 | 0 | 0 | -147,-174,MeWo | 0000 | 0000 | 0000 |
| Choriocarcinomas | | | | Astrocytomas | | | |
| GCC-SV(c),-MM,Lu75(c),SCH, | 0000 | 0000 | 0●●0 | SK-MG-1,-2,-3,-4,-6,-7, | 00000 | 00000 | 00000 |
| BeWo,JAR,JEG-3 | 000 | 000 | ●●● | -12,-13,-14,-16,-17, | 00000 | 00000 | 00000 |
| Breast Cancers | | | | U251MG,U373MG | 000 | 000 | 000 |
| MCF-7,CAMA,BT-20,-474, | 0000 | 0000 | ●●0● | Retinoblastomas | | | |
| AlAb,ZR-75-1,SK-BR-3,-5,-7, | 00000 | 00000 | ●●●●0 | Y79,WERI | 00 | 00 | 0● |
| MDA-MB-134,-157,-231,-361 | 0000 | 0000 | ●000 | Neuroblastomas | | | |
| Ovarian Cancers | | | | SK-N-SH,-MC,-BE(2), | 00000 | 00000 | ●●0●● |
| SK-OV-3,-2774,SW626, | 0000 | 0000 | 0●● | CHP234,LA-N-1,-2, | 0000 | 0000 | ●●●0 |
| Colo316,ROAC,SK-OV- | 00 | 00 | 0● | SMS-MSN,-SAN,-KAN | | | |
| Uterus/Cervix Cancers | | | | T-cell lymphomas/leukemias | | | |
| SK-UT-1,ME180 | 00 | 00 | ●0 | MOLT-4,T45,HPB-ALL,CCRF- | 0000 | 0000 | 0●●● |
| Colon Cancers | | | | CEM,P12/Ichikawa | 0 | 0 | ● |
| SW-48,-403,-480,-620, | 0000 | 0C●0 | ●0●● | B-cell lymphomas/leukemias | | | |
| -1222,-1417,CaCo2,HT29, | 0000 | 0000 | ●0●0 | SK-DHL-2,-10,SK-LY-16, | 0000 | 0000 | ●000 |
| SK-CO-10,-11,-13,-15 | 0000 | 0000 | 000● | -18,RAJI,BALL-1,ARA-10 | 000 | 000 | 000 |
| Gastric/Liver/Pancreas Cancers | | | | Null cell leukemias | | | |
| MKN45,SK-HEP-1,AsPc-1 | 000 | 000 | 000 | NALL-1, NKL-1,-2, | 0000 | 0000 | ●●●0 |
| | | | | NALM-1,-16 | 0 | 0 | 0 |
| Cells | AbK4 | AbK21 | AbP12 | Cells | AbK4 | AbK21 | AbP12 |
| Lung Cancers | | | | Myeloid/monocytic leukemias | | | |
| SK-LC-1,-2,-3,-5,-6, | 00000 | 00000 | 000●● | HL60,K562,U937 | 000 | 000 | ●0● |
| -7,-8,-10,-12,-13, | 00000 | 00000 | ●0●0● | Myeloma | | | |
| -14,-15,-16,-17,-LL, | 00000 | 00000 | 00C●0 | SK-MY-1 | 0 | 0 | 0 |
| Calu-1,-4 | 00 | 00 | 0● | Normal Cells | | | |
| Renal Cancers | | | | Kidney epithelium | 0XXX0 | ●●●●● | ●●●●● |
| SK-RC-1,-2,-4,-6,-9, | 00000 | 00●●0 | ●●000 | Skin Fibroblasts | 00000 | 00000 | 0XXX0 |
| -20,-28,-29,-31,-34, | 00000 | 0●●●0 | 0●●00 | EBV-transformed B-cells | 00000 | 00000 | ●●000 |
| -37,-38,-39,-41,-44, | 00000 | ●0●●● | 00●●● | Erythrocytes (A,B,O) | 0 | 0 | ● |
| -45,Caki-1 | 00 | ●● | ●● | Erythrocytes, | 0 | 0 | |
| Bladder Cancers | | | | neuraminidase treated | | | |
| T24,RT4,TCCSUP,SCABER, | 0000 | 0000 | 0000 | | | | |
| VM-CUB-1,-2,-3,5637, | 0000 | 0000 | 0000 | | | | |
| SW-800,-1710,639V,647V | 0000 | 0000 | 0●00 | | | | |
| Prostate Cancers | | | | | | | |
| KNS62,DU145 | 00 | 00 | 0● | | | | |

TABLE 2

Immunofluorescence staining of human tissues with monoclonal antibodies.

| Tissue | Monoclonal antibody[a] K4 F | K4 A | K21 F | K21 A | P12 F | P12 A | Tissue | K4 F | K4 A | K21 F | K21 A | P12 F | P12 A |
|---|---|---|---|---|---|---|---|---|---|---|---|---|---|
| Urogenital system | | | | | | | Endocrine glands | | | | | | |
| Testis | 0 | 0 | 0 | 0 | 0 | 0 | Thyroid | 0 | 0 | 0 | 0 | 0 | 0 |
| Ovary | 0 | 0 | 0 | 0 | 0 | 0 | Adrenal | 0 | 0 | 0 | 0 | 0 | 0 |
| Uterus | | 0 | | 0[b] | | 0 | Pancreas | 0 | 0 | 0 | 0 | 0 | 0 |
| Cervix | | 0 | | 0 | | 0 | Cardiovascular system | | | | | | |
| Kidney | 0 | 0 | 0 | 0[c] | ● | ●[d] | Heart | 0 | 0 | 0 | 0 | 0 | 0 |
| Urothelium | 0 | 0 | 0 | 0 | ● | ● | Blood vessels | 0 | 0 | 0 | 0 | 0 | 0 |
| Placenta | ● | | 0 | | 0 | | Thymus | ● | | 0 | | 0 | |
| Mammary gland | | 0 | | 0 | ● | ●[e] | Spleen | ● | 0 | 0 | 0 | ● | ● |
| Respiratory system | | | | | | | Lymphocytes | 0 | 0 | 0 | 0 | 0 | 0 |
| Bronchi | 0 | 0 | ● | 0 | 0 | 0 | Granulocytes | 0 | 0 | 0 | 0 | ● | ● |
| Lung | 0 | 0 | 0 | 0 | 0 | 0 | Erythrocytes | 0 | 0 | 0 | 0 | 0 | 0 |
| Digestive system | | | | | | | Nervous system | | | | | | |
| Esophagus | 0 | 0 | 0 | 0 | ● | 0 | Brain[f] | 0 | 0 | 0 | 0 | 0 | 0 |
| Stomach | ● | ● | ● | 0 | ● | ● | Spinal cord | 0 | 0 | 0 | 0 | 0 | 0 |
| Small intestine | ● | ● | ● | 0 | ● | ● | Peripheral nerves | 0 | 0 | 0 | 0 | 0 | 0 |
| Colon | | | | 0 | | | | | | | | | |
| Liver | 0 | 0 | 0 | 0 | 0 | 0 | | | | | | | |
| Pancreas | 0 | 0 | 0 | 0 | 0 | 0 | | | | | | | |
| Skin | 0 | 0 | 0 | 0 | 0 | 0 | | | | | | | |

TABLE 3

Immunofluorescence staining of human tumor tissues with monoclonal antibodies.

| Tumor type | K4* | K21 | P12 |
|---|---|---|---|
| Testicular Teratocarcinoma | 8/9 | 6/9 | 6/9 |
| Renal cancer | 0/5 | 1/7 | 0/5 |
| Colon cancer | 2/4 | 0/4 | 4/4 |
| Bladder cancer | 1/5 | 0/5 | 4/5 |
| Breast cancer | ½ | 0/4 | 4/4 |
| Lung cancer | 0/4 | 0/4 | 2/4 |
| Astrocytoma | ½ | 0/2 | ½ |
| Melanoma | 0/2 | 0/2 | 0/2 |
| Lymphoma | 0/2 | 0/2 | ½ |

*Fractions indicate the number of antigen-positive tumor specimens per total number of specimens tested with the antibody.

FIG. 1.

Analysis of binding of monoclonal antibodies to glycoproteins, glycolipids, and synthetic glycoproteins using a solid phase enzyme-linked immunoassay (ELISA). Top left: AbP12 binding to glycolipids; bottom left: AbP12 binding to blood group glycoprotiens; top center: AbK4 binding to glycolipids; bottom center: AbK4 binding to blood group glycoproteins; top right: AbK21 binding to synthetic glycoproteins; bottom left: AbK21 binding to blood group glycoproteins. Glycolipids (top left and top center) - ∇: αFuc(1→2)βGal(1→4)βGlcNAc (1→3)62 Gal(1→4)Glc-Cer(H-5-2); Δ: αFuc(1→2)βGal(1→3)βGlcNAc(1→3)βGal(1→4)Glc-Cer(H-5-1); 0: αGal(1→4)βGlcNAc(3←1Fucα) (1→3)βGal(1→4)Glc-Cer(X-5); 0: βGal(1→3)βGlcNAc(4←1Fucα)(1→3)βGal(1→4)Glc-Cer(Le[a]-5); □ αFuc(1→2)β-Gal(1→4)βGlcNAc (3←1Fucα)(1→3)βGal(1→4)Glc-Cer(Y-6); ∨ αFuc(1→2)βGal(1→3) βGlcNAc(4←1-Fucα)(1→3)βGal(1→4)Glc-Cer(Le[b]- 6). LNT-Cer and LNneoT-Cer were also tested and were unreactive with AbP12, AbK4 and AbK21. Blood group glycoproteins (bottom left, center and right) - VL Le[a] (N-1); 0: precursor substance (OG); □: H Le[b] (Tighe); ∇: B (Beach); Δ: Hog mucin Smith degraded substance; 0: A (MSS). Synthetic glycoproteins (top right) - 0: LNT-BSA; 0: LNneoT-BSA; ∇: αNANA(2→6) LNneoT-BSA.

Fluorographs of immunoprecipitates obtained with monoclonal antibodies analyzed on SDS-polyacrylamide gels.

A. [³H] glucosamine-labeled extract of Tera-1 cells precipitated with AbK4 (lane 1) or an unrelated monoclonal antibody of IgG1 subclass (lane 2).

B. [³⁵S]O₄ labeled extract of Tera-2 cells heated to 100° C. for 5' and precipitated with AbK4 (lane 1) or control antibody (lane), lane 3: K4 immunoprecipitates treated with chondroitinase ABC prior to SDS-PAGE, lane 4: AbK4 precipitation of neuraminidase-treated cell extract.

C. [³⁵S]O₄ labeled extract of Tera-2 cells, precipitated with AbK21 (lane 1: 12 hr exposure, lane 4: 5d exposure), and neuraminidase treated extract precipitated with AbK21 (lane 2: 12 hr exposure). Lane 3: precipitation with an unrelated antibody of IgM subclass. Lanes 5-9: sequential immunoprecipitation: [³⁵O]₄-labeled Tera-2 extracts were incubated with antibody I, immunoprecipitates were bound with Staphylococcus aureus protein A and isolated for SDS-PAGE analysis by centrifugation and supernatants were used for immunoprecipitation with antibody II. Lane 5: work precleaning with unrelated IgG1 (antibody I), AbK21 (II); lane 6: AgK21(I), AbK21 (II) Lane 7: AbK4 (I); AbK4(II), lane 8: AbK21(I); AbK4(II); lane 9: work precleaning with unrelated IgM antibody (I) precipitation with AbK4 (II).

D. [³H] fucose labeled MCF-7 cell extract precipitated with AbP12 (lane 1) or normal nu/nu mouse serum (lane 2).

FIG. 2

Fluorographs of immunoprecipitates obtained from radiolabeled cell extracts with mouse monoclonal antibodies analyzed by SDS-PAGE. Tera-1 teratocarcinoma cells were labeled with [³H]glucosamine (lanes A and B), Tera-2 cells were labeled with [³⁵S]O₄ (lanes C-E and H-M) and MCF-7 breast cancer cells were labeled with [³H]fucose (lanes F and G). Monoclonal antibodies used for immunoprecipitation tests were - Lane A: AbK4. Lane B: unrelated IgGI antibody. Lane C: AbK21. Lane D: AbK21 (with neuraminidase-treated cell extract). Lane E: unrelated IgM antibody. Lane F: AbP12. Lane G: unrelated IgM antibody. Lane H: AbK4 (with cell extract mock-precleared with unrelated IgM antibody). Lane I: AbK4 (with cell extract precleared with AbK4). Lane J: AbK4 (with cell extract precleared with AbK21). Lane K: AbK4 (with neuraminidasetreated cell extract). Lane L: AbK4 (with cell extract heated to 100° C. for 5 min prior to incubation with antibody). Lane M: AbK4 (with cell extract treated with chondroitinase ABC after immunoprecipitation). Molecular weight markers used were: myosin (200,000), β-galactosidase (120,000), phosphorylase a (98,000), bovine serum albumin (68,000) and ovalbumin (43,000).

What is claimed:

1. A hybridoma cell line deisgnated K4 (ATCC No. HB8550).

2. A monoclonal antibody produced by the hybridoma cell line of claim 1.

3. A method of differentiating between normal and cancerous human cells which comprises contacting a cell sample with the monoclonal antibody of claim 2 and observing reactions between the cells and the monoclonal antibody.

4. A method of claim 3, wherein the monoclonal antibody is labelled with a fluorescent, radioactive or chromophoric group.

5. A method of detecting human tumor cells or antigens therefore in a sample which comprises contacting the sample with the monoclonal antibody of claim 2 and observing reactions between the cells and the monoclonal antibody.

6. A method of claim 5, wherein the monoclonal antibody is labelled with a fluorescent, radioactive or chromophoric group.

* * * * *